United States Patent [19]

Chang et al.

[11] Patent Number: 4,870,192
[45] Date of Patent: Sep. 26, 1989

[54] PRODUCTION OF LACTONES AND OMEGA-HYDROXYCARBOXYLIC ACIDS

[75] Inventors: Clarence D. Chang, Princeton; Stuart D. Hellring, Trenton, both of N.J.

[73] Assignee: Mobil Oil Corporation, New York, N.Y.

[21] Appl. No.: 918,683

[22] Filed: Oct. 14, 1986

Related U.S. Application Data

[63] Continuation of Ser. No. 764,358, Aug. 12, 1985, abandoned.

[51] Int. Cl.$^4$ ............... C07D 313/04; C07D 309.04; C07C 51/245
[52] U.S. Cl. ................................. 549/272; 549/273; 562/528
[58] Field of Search ................ 549/272, 273; 562/528

[56] References Cited

U.S. PATENT DOCUMENTS

| Re. 29,948 | 3/1979 | Dwyer et al. | 208/110 |
|---|---|---|---|
| 3,064,008 | 11/1962 | Phillips et al. | 260/343 |
| 3,428,656 | 2/1969 | Weiss et al. | 260/343 |
| 3,483,222 | 12/1969 | Sennewald et al. | 260/343 |
| 3,517,033 | 6/1970 | Weiberg | 260/343 |
| 3,590,080 | 6/1971 | Beesley et al. | 260/535 |
| 3,728,358 | 4/1973 | Mookherjee et al. | 260/343 |
| 3,833,613 | 9/1974 | Field | 260/343 |
| 4,013,691 | 3/1977 | Maki et al. | 260/343 |
| 4,171,313 | 10/1979 | Mares et al. | 260/343 |
| 4,213,906 | 7/1980 | Mares et al. | 260/343 |
| 4,284,529 | 8/1981 | Shihabi | 502/71 |
| 4,286,068 | 8/1981 | Mares et al. | 521/53 |
| 4,353,832 | 10/1982 | Lecloux et al. | 549/272 |

FOREIGN PATENT DOCUMENTS 100119 2/1984 European Pat. Off. ............ 549/531

OTHER PUBLICATIONS

Kirk–Othmer Encyclopedia of Chemical Technology, vol. 15 (Molecular Sieves) pp. 638 and 649.

Primary Examiner—Glennon H. Hollrah
Assistant Examiner—Ba Trinh
Attorney, Agent, or Firm—Alexander J. McKillip; Charles J. Speciale; Marina V. Schneller

[57] ABSTRACT

This invention provides process embodiments for shape-selective oxidation of cyclic ketones to lactone and/or omega-hydroxycarboxylic acid products in the presence of a zeolite catalyst composition such as ZSM-5 or zeolite Beta.

Cyclohexanone can be converted to epsilon-caprolactone or 6-hydroxycaproic acid as a main product under selected conditions.

15 Claims, No Drawings

PRODUCTION OF LACTONES AND OMEGA-HYDROXYCARBOXYLIC ACIDS

This is a continuation of copending application Ser. No. 764,358, filed on Aug. 12, 1985, now abandoned.

BACKGROUND OF THE INVENTION

Percarboxylic acids are utilized to oxidize cyclic ketones to lactones and omega-hydroxycarboxylic acids under Baeyer-Villiger conditions [Ber., 32, 3625 (1899); 33, 858 (1900)]. This procedure requires the preliminary preparation of the percarboxylic acid reagent; and the presence of the percarboxylic acid and the corresponding carboxylic acid byproduct results in the formation of undesirable derivatives of these carboxylic acid reactants.

As an alternative procedure, hydrogen peroxide has been substituted for percarboxylic acid. Hydrogen peroxide is unreactive unless it is in combination with a catalyst such as an oxyacid of Group IV-VI metal. A main disadvantage of the hydrogen peroxide route is the need for a large quantity of the catalyst component.

U.S. Pat. No. 3,064,008 describe a process for oxidizing cyclohexanone to epsilon-caprolactone with peracetic acid or acetaldehyde monoperacetate. Other prior art which describe conversion of cyclic ketones to lactones and/or omega-hydroxycarboxylic acids with an organic peracid or hydroperoxide include U.S. Pat. Nos. 3,517,033; 3,728,358; 3,833,613; and 3,483,222.

U.S. Pat. No. 4,013,691 describes a process for oxidizing cyclohexanone with molecular oxygen in the presence of an aldehyde, a soluble compound of a Group VIII type metal, and a ligand compound to produce epsilon-caprolactone.

Of more specific interest with respect to the present invention is prior art relating to oxidation of cyclic ketones to lactones and omega-hydroxycarboxylic acids with hydrogen peroxide and various catalyst systems. Pertinent United States patents include 3,428,656; 3,590,080; 4,171,313; 4,213,906; 4,286,068; and 4,353,832.

There is continuing interest in the development of new and improved processes for the production of lactones and omega-hydroxycarboxylic acids from cyclic ketone starting materials.

Accordingly, it is an object of this invention to provide a process for converting a cyclic ketone to lactone and omega-hydroxycarboxylic acid products by oxidation under Baeyer-Villiger conditions in the presence of a zeolite catalyst.

It is another object of this invention to provide a process for converting a cyclic ketone to a lactone product by shape-selective oxidation with hydrogen peroxide in the presence of a zeolite catalyst having a Constraint Index between about 0.4-10.

It is a further object of this invention to provide a process for converting a cyclic ketone to an omega-hydroxycarboxylic acid product by shape-selective oxidation with hydrogen peroxide in the presence of a zeolite catalyst having a Constraint Index between about 1-12.

Other objects and advantages of the present invention shall become apparent from the accompanying description and examples.

DESCRIPTION OF THE INVENTION

One or more objects of the present invention are accomplished by the provision of a process for the production of lactone and omega-hydroxycarboxylic acid products which comprises reacting a cyclic ketone with hydrogen peroxide at a temperature between about −20° C. and 100° C. in the presence of a zeolite catalyst.

In another embodiment, this invention provides a process for shape-selective oxidation of cyclopentanone which comprises reacting cyclopentanone with hydrogen peroxide at a temperature between about −20° C. and 60° C. in a liquid phase reaction medium in the presence of a zeolite catalyst having a Constraint Index between about 2-10 and a silica/alumina ratio greater than about 70, and producing a product comprising delta-valerolactone.

In another embodiment, this invention provides a process for shape-selective oxidation of cyclopentanone which comprises reacting cyclopentanone with hydrogen peroxide at a temperature between about 0° C. and 100° C. in a liquid phase reaction medium in the presence of a zeolite catalyst having a Constraint Index between about 0.4-12 and a silica/alumina ratio between about 1-70, and producing a product comprising 5-hydroxyvaleric acid.

In another embodiment, this invention provides a process for shape-selective oxidation of cyclohexanone which comprises reacting cyclohexanone with hydrogen peroxide at a temperature between about −20° C. and 60° C. in a liquid phase reaction medium in the presence of a zeolite catalyst having a Constraint Index between about 1-9 and a silica/alumina ratio greater than about 70, and producing a product comprising epsilon-caprolactone.

In a further embodiment, a process for shape-selective oxidation of cyclohexanone which comprises reacting cyclohexanone with hydrogen peroxide at a temperature between about 0° C. and 100° C. in a liquid phase reaction medium in the presence of a zeolite catalyst having a Constraint Index between about 0.4-10 and a silica/alumina ratio between about 1-70, and producing a product comprising 6-hydroxycaproic acid.

Cyclic ketones which are suitable as starting materials for the present invention process embodiments include cyclobutanone, cyclopentanone and cyclohexanone, and the corresponding cyclic ketone structures containing one or more ring substituents such as methyl, ethyl, methoxy, chloro, nitro, hydroxy, dimethylamino, phenyl, cyclohexyl, and the like.

A cyclic ketone starting material must have a dimensional conformation which permits the cyclic ketone molecules to enter into the pore structure of the zeolite catalyst utilized in a process embodiment. "Shape-selective oxidation" refers to the reaction between a cyclic ketone starting material and hydrogen peroxide that occurs within the pore substrate of the zeolite catalyst.

The present invention process is operated at a reaction temperature selected within the broad range between about −20° and 100° C., depending on which process embodiment is being employed to produce a desired compound as the major product. The invention process can be conducted conveniently under ambient pressure.

The reaction time will vary between about 0.5-10 hours for a batch type reaction procedure. For a continuous reaction system such as with a fixed bed reaction zone, a typical liquid hourly space velocity (LHSV) will be in the range between about 0.1–10.

The hydrogen peroxide reagent is employed in the form of a solution, e.g., in a concentration between about 20–85 weight percent of hydrogen peroxide. The solution medium can be water or an organic solvent such as acetonitrile or dioxane.

The hydrogen peroxide is employed in a quantity between about 0.1–5 moles of hydrogen peroxide per mole of cyclic ketone starting material, as determined by such factors as the mode of contact between the reactants, the reaction temperature, the reactivity of the cyclic ketone, and the like.

Preferably, in a batch mode one of the reactants is added slowly to the other reactant in the reaction zone containing the zeolite catalyst. In a continuous process, each of the cyclic ketone and hydrogen peroxide reactants is introduced separately and simultaneously into the reaction zone.

If the desired product is a lactone, then the yield of lactone product is favored by the limitation or absence of water in the reaction medium. Essentially anhydrous conditions can be achieved by employing hydrogen peroxide as a solution in an organic solvent, and by removing water byproduct continuously by azeotropic distillation during the course of the oxidation reaction.

An organic solvent can be employed as a diluent or reaction medium in the invention process. The organic solvent can be either water-miscible or water-immiscible. In a process embodiment which employs water as a liquid phase reaction medium component, the use of a water-miscible solvent usually will result in a two-phase reaction system (i.e., a solid zeolite catalyst and a homogeneous aqueous solution), and the use of a water-immiscible solvent results in a three-phase reaction system (i.e., a solid zeolite catalyst, a water phase, and an organic solvent phase).

Illustrative of solvents are acetonitrile, dioxane, tetrahydrofuran, acetone, ethanol, pentane, cyclohexane, benzene, toluene, nitromethane, methylene chloride, chloroform, carbon tetrachloride, dichloroethane, trichloroethylene, chlorobenzene, nitrobenzene, and the like. The solvent generally is employed in a quantity between about 20–80 weight percent of the liquid phase reaction medium.

An essential aspect of the invention process is the presence of a zeolite catalyst composition in the reaction medium. The zeolite catalyst provides a shape-selective constrained access to and egress from the intracrystalline free space by virtue of having an effective pore size. The cyclic ketone and hydrogen peroxide interact within the pore structure of the zeolite catalyst, and shape-selective oxidation of cyclic ketone to lactone and/or omega-hydroxycarboxylic acid products occurs.

The shape-selective activity of the zeolite catalyst composition relates to a specific property of the crystalline zeolite structure, i.e., the Constraint Index.

As described in U.S. Pat. No. 4,284,529 (incorporated by reference), a simple determination of the "Constraint Index" is accomplished by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 40° C. for at least 15 minutes. The zeolite is then flushed with helium and the temperature is adjusted between 290° C. and 510° C. to give an overall conversion of 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is analyzed, e.g., by gas chromatography, to determine the fraction remaining unchanged for each of the two hydrocarbons.

The Constraint Index is calculated as follows:

$$\text{Constraint Index} = \frac{\log (\text{fraction of hexane remaining})}{\log (\text{fraction of 3-methylpentane remaining})}$$

The Constraint Index approximates the ratio of the cracking rate constants for the two hydrocarbons. Zeolites suitable for the present invention process are those having a Constraint Index of 0.4–12. Constraint Index (C.I.) values for some typical zeolite materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon(mordenite) | 0.4 |
| REY | 0.4 |
| Amorphous Silica-Alumina | 0.6 |
| Erionite | 38 |

Zeolite compositions of intermediate pore size suitable for the invention process include ZSM-5, ZSM-11 and ZSM-23.

Zeolite compositions of large pore size suitable for the invention process include zeolite Beta, mordenite and zeolite Y.

A small pore zeolite composition such as erionite has a Constraint Index of about 38, and is not suitable for the shape-selective oxidation process embodiments of the present invention.

ZSM-5 is described in U.S. Pat. No.3,702,886 and U.S. Pat. No. Re. 29,948, incorporated by reference.

ZSM-11 is described in U.S. Pat. No. 3,709,979, incorporated by reference.

ZSM-23 is described in U.S. Pat. No. 4,076,842, incorporated by reference.

Zeolite Beta is described in U.S. Pat. No. 3,308,069, incorporated by reference.

Zeolon (synthetic mordenite) is described in U.S. Pat. No. 3,334,964, incorporated by reference.

Zeolite Y is described in U.S. Pat. No. 3,130,007, incorporated by reference.

Other suitable zeolite compositions include ZSM-12 (U.S. Pat. No. 3,832,449), ZSM-35 (U.S. Pat. No. b 4,016,245), ZSM-38 (U.S. Pat. No. 4,046,859), and ZSM-48 (U.S. Pat. No. 4,375,573), incorporated by reference. These zeolites have a Constraint Index in the range between about 2–5.

In addition to Constraint Index, a zeolite catalyst composition utilized in the invention process is characterized by another important property, i.e., the zeolite has a silica/alumina ratio greater than about 70 for process embodiments directed to the production of a lactone as the main product, and the zeolite has a silica/alumina ratio between about 1-70 for process embodiments directed to the production of an omega-hydroxycarboxylic acid as the main product.

As the silica/alumina ratio of a zeolite composition increases, the intracrystalline pore surfaces of the zeolite substrate become less acidic and more hydrophobic with respect to a content of reactant species.

As disclosed in U.S. Pat. No. 4,351,979, the acid activity of a zeolite catalyst is conveniently defined by the "Alpha" scale described in an article published in Journal of Catalysis, Vol. VI, pp 278-287 (1966), incorporated herein by reference. In this test, the zeolite catalyst is contacted with hexane under prescribed conditions and the amount of hexane which is cracked is measured. The Alpha value is computed from this measurement.

For purposes of the present invention process, a zeolite catalyst composition with an Alpha value less than about 20 favors the formation of a lactone product, and a zeolite catalyst composition with an Alpha value greater than 20 favors the formation of an omega-hydroxycarboxylic acid product.

If a metal such as iron, palladium or platinum is ion-exchanged into a zeolite catalyst composition to function as a promoter for the present invention oxidation reaction, the 20 metal is incorporated in a quantity between about 0.05-10 weight percent, based on the zeolite catalyst weight.

In a further embodiment, a metal such as iron, cobalt, vanadium or manganese can be incorporated in a zeolite catalyst composition as framework elements.

A zeolite catalyst composition is employed in the invention process in a quantity between about 0.5-50 weight percent, based on the weight of cyclic ketone in the reaction medium.

After the completion of the oxidation reaction period, the lactone and/or omega-hydroxycarboxylic acid products and unreacted cyclic ketone are recovered by conventional procedures, such as fractional distillation.

In the practice of the invention process, typically about 40-90 percent of the cyclic ketone is oxidized, and the selectivity to lactone and/or omega-hydroxycarboxylic acid products are at least about 80 percent.

The present invention process has several advantages over prior art catalytic methods for oxidation of cyclic ketones under Baeyer-Villiger conditions.

A zeolite catalyst composition has unique properties. It achieves shape-selective oxidation of cyclic ketones with hydrogen peroxide, and the intracrystalline spaces where the oxidation reaction occurs are less subject to catalyst poisoning and deactivation. Further, a zeolite catalyst composition such as ZSM-5 is stable and is easily regenerated to its original reactivity by a conventional calcination procedure.

Another important advantage of the invention process is that reaction conditions can be controlled to produce a desired product, such as either a lactone or an omega-hydroxycarboxylic acid as the main product, or a lactone/omega-hydroxycarboxylic acid product mixture in a controlled molar ratio of the constituents.

In general, the formation of lactone product in the invention process is enhanced by a low reaction temperature, a short reaction time, a low conversion of cyclic ketone, a minimal presence of water in the reaction medium, and a zeolite catalyst composition having a low Constraint Index and a high silica/alumina ratio.

The formation of omega-hydroxycarboxylic acid product is enhanced by a high reaction temperature, a long reaction time, a high conversion of cyclic ketone, the presence of water in the reaction medium, and a zeolite catalyst composition having a high Constraint Index and a low silica/alumina ratio.

If in a process embodiment a catalyst Constraint Index is selected which is too low to effect the desired shape-selective oxidation of ketone starting material, then the production of omega-hydroxycarboxylic acid is favored over the competing lactone product. For each of the cyclopentanone and cyclohexanone starting materials there appears to be an intermediate Constraint Index range for each zeolite catalyst composition which favors lactone product formation and accumulation. If the Constraint Index value is above or below the intermediate range, then the formation of omega-hydroxycarboxylic acid is favored over the lactone product.

The present invention further contemplates the production of a zeolite composition which has incorporated a peroxy-silica/alumina structure:

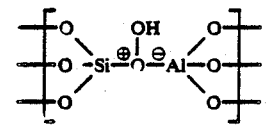

The peroxy-zeolite composition can be produced by treating a zeolite with a hydrogen peroxide solution. The peroxy-zeolite can be recovered as a dry solid product, and employed as a selective oxidizing agent or as a free radical initiating agent.

The following examples are further illustrative of the present invention. The components and specific ingredients are presented as being typical, and various modifications can be derived in view of the foregoing disclosure within the scope of the invention.

EXAMPLE I

This Example illustrates the preparation of HZSM-5 zeolite catalyst compositions. The following materials are employed:

| |
|---|
| Silicate Solution |
| 42.2 lb. Q-brand Sodium Silicate (Na$_2$O/SiO$_2$ = 3.3) |
| 52.2 lb Water |
| Acid Solution |
| 612 grams Aluminum Sulfate |
| 1600 grams Sulfuric Acid |
| 7190 grams Sodium Chloride |
| 72.2 lb Water |
| Organics |
| 1290 grams Tri-n-propylamine |
| 1110 grams n-Propylbromide |

The silicate solution and acid solution are nozzle mixed to form a gelatinous precipitate that is charged to a 30 gallon stirred autoclave. When gelation is complete, the organics are added and the temperature raised to 155° C. with agitation. The reaction mixture is held at 155° C. with an agitation rate of 121 RPM for 17 hours. The product at this time is analyzed by X-ray diffraction to confirm the ZSM-5 structure.

The product is washed free of soluble salts and dried. The product has the following analysis:

| | |
|---|---|
| Al$_2$O$_3$ | 1.0 |
| SiO$_2$ | 74.4 |
| Na$_2$O | 0.31 |
| N | 2.26 |
| C | 21.9 |

The ZSM-5 is precalcined in air at 370° C. and thereafter ammonium exchanged by contacting twice with 5N NH$_4$Cl solution at 100° C. (15 ml per gram zeolite), then filtered, washed free of chloride and air dried.

The resulting ammonium form of ZSM-5 is converted to the hydrogen form by calcination in air at 1° C/minute to 538° C and then held at 538° C. for 10 hours.

The HZSM-5 catalyst composition(I) is ball milled for two hours to form a fine powder. The fine powder is screened to the desired particle size range, e.g., 100–200 mesh.

A larger particle size range is obtained by pelleting the powder, and then crushing the pellets to a desired particle size range, e.g., 50–100 mesh.

A Cu-Zn/HZSM-5 catalyst composition is prepared by treating the above described HZSM-5 catalyst composition(I) with 0.1N Cu(NO$_3$)$_2$ solution twice at 800° C. for one hour each, using 5 ml of solution per gram of catalyst per ion-exchange cycle. The resultant composition is then ion-exchanged with 0.1 N Zn(NO$_3$)$_2$. The washed and dried catalyst is slugged, crushed, and sized by screening. After calcination at 538° C. for three hours, the catalyst is found to contain 0.25% copper and 1% zinc by weight.

In a similar manner, the HZSM-5 catalyst composition(I) described above is impregnated with a calculated amount of H$_2$PtCl$_6$ solution to give 0.1% by weight of platinum in the final product. The resultant composition is calcined at 538° C. in air for 3 hours.

Other catalyst compositions are prepared in a similar manner by employing ZSM-11 and ZSM-23 zeolite substrates, respectively, instead of ZSM-5.

EXAMPLE II

This Example illustrates the production of delta-valerolactone in accordance with the present invention.

Cyclopentanone (0.95 ml) is added to a reactor containing a suspension of dichloromethane (5 ml), 30% aqueous hydrogen peroxide (5 ml), ZSM-5 (proton-form, silica/alumina=70), and biphenyl 0.05 g) as an internal standard. After stirring for 5 hours at ambient temperature, analysis by gas chromatography indicates 40% conversion and 25 weight percent delta-valerolactone (62.5% selectivity).

Product assignment is confirmed by comparing gas chromatography/mass spectroscopy data with that of an authentic commerical sample.

The conversion selectivity to delta-valerolactone is improved if the reaction period is two hours instead of five hours, and the conversion of cyclopentanone is lower.

EXAMPLE III

This Example illustrates the selective production of 5-hydroxypentanoic acid in accordance with the present invention.

Cyclopentanone (0.95 ml) is added to a reactor containing a mixture of dichloromethane (5 ml), 30% aqueous hydrogen peroxide (5 ml), Zeolon H (0.5 g, silica/alumina=10), and biphenyl (0.05 g) as an internal standard. After stirring 7.2 hours at ambient temperature, gas chromatography analysis indicated 49% conversion, and 2.3 weight percent of delta-valerolactone product.

The reaction mixture is filtered and the immiscible liquid phases are separated. The aqueous phase is extracted with ether, and the combined organic media are stirred overnight with 25% aqueous sodium metabisulfite to remove peroxides. The resultant mixture is separated, and the bisulfite solution is extracted with ether. After drying over anhydrous MgSO$_4$, the combined organic phases give a negative peroxide test (starch-iodine), and are then concentrated under vacuum to provide 5-hydroxypentanoic acid (0.45 g, 34% yield, 66% selectivity).

The product structure is verified by comparing gas chromatography/mass spectroscopy data with that of a sample prepared by aqueous acid hydrolysis of a commercial sample of delta-valerolactone.

The conversion selectivity to 5-hydroxypentanoic acid is improved if a temperature of 40° C. is employed instead of an ambient temperature of about 25° C.

EXAMPLE IV

This Example illustrates the selective production of epsilon-caprolactone in accordance with the present invention.

Cyclohexanone (0.95 ml) is added to a reactor containing a suspension of dichloromethane (5 ml), 30% aqueous hydrogen peroxide (5 ml), ZSM-5 (proton-form, silica/alumina=70), and biphenyl (0.05 g) as an internal standard. After stirring at ambient room temperature for one hour, analysis by gas chromatography indicates 5.6% conversion, and 4.2% of epsilon-caprolactone (75% selectivity). Product assignment is confirmed by comparison of gas chromatography/mass spectroscopy data from an authentic commercial sample.

The conversion of cyclohexanone is higher if the reaction period is increased from one hour to three hours.

The conversion selectivity to epsilon-caprolactone is improved if the ZSM-5 zeolite has a silica/alumina ratio of about 500 instead of about 70.

EXAMPLE V

This Example illustrates the selective production of 6-hydroxycaproic acid in accordance with the present invention.

Cyclohexanone (0.95 ml) is added to a reactor containing a suspension of dichloromethane (5 ml), 30% aqueous hydrogen peroxide (5 ml), ZSM-5 (proton-form, silica/alumina=70), and biphenyl (0.05 g) as an internal standard. After stirring at ambient temperature for 8 hours, analysis by gas chromatography indicates 44% cyclohexanone conversion, and 8.8 weight percent epsilon-caprolactone product.

The reaction mixture is filtered and the liquid phases separated. The aqueous phase is extracted with ether, and the combined organic media are stirred overnight with 25% aqueous sodium metabisulfite to remove peroxides. The immiscible phases are separated, and the aqueous bisulfite solution is extracted with ether. After drying over anhydrous MgSO$_4$, the combined organic media give a negative peroxide test (starch-iodine), and then are concentrated under vacuum to provide 6-hydroxycaproic acid as a pale yellow solid (0.4 g, 30% yield, 68% selectivity). The product structure is verified by comparison of IR spectra with that of a sample prepared by aqueous acid hydrolysis of a commercial sample of epsilon-caprolactone.

What is claimed is:

1. A process for shape-selective oxidation of cyclopentanone which comprises reacting cyclopentanone with hydrogen peroxide at a temperature between about $-20°$ C. and $60°$ C. in a liquid phase reaction medium in the presence of a catalyst consisting of a zeolite having a Constraint Index between about 2-10 and a silica/alumina ratio greater than about 70, and producing a product comprising delta-valerolactone.

2. A process in accordance with claim 1 wherein the zeolite is ZSM-5.

3. A process in accordance with claim 1 wherein the liquid phase medium includes a water-immiscible organic solvent.

4. A process in accordance with claim 1 wherein the liquid phase reaction medium contains less than about 5 weight percent of water.

5. A process for shape-selective oxidation of cyclopentanone which comprises reacting cyclopentanone with hydrogen peroxide at a temperature between about $0°$ C. and $1000°$ C. in a liquid phase reaction medium in the presence of a zeolite catalyst having a Constraint Index between about 0.4-12 and a silica/alumina ratio between about 1-70, and producing a product comprising 5-hydroxyvaleric acid.

6. A process in accordance with claim 5 wherein the zeolite catalyst is ZSM-5.

7. A process in accordance with claim 5 wherein the liquid phase reaction medium includes a water-immiscible organic solvent.

8. A process in accordance with claim 5 wherein the liquid phase reaction medium contains between about 5-30 weight percent of water.

9. A process for shape-selective oxidation of cyclohexanone which comprises reacting cyclohexanone with hydrogen peroxide at a temperature between about -31 $20°$ C. and $60°$ C. in a liquid phase reaction medium in the presence of a catalyst consisting of a zeolite having a Constraint Index between about 1-9 and silica/alumina ratio greater than about 70, and producing product comprising epsilon-caprolactone.

10. A process in accordance with claim 9 wherein the zeolite catalyst is ZSM-5.

11. A process in accordance with claim 9 wherein the liquid phase reaction medium includes a water-immiscible solvent.

12. A process in accordance with claim 9 wherein the liquid phase reaction medium contains less than about 5 weight percent of water.

13. A process for shape-selective oxidation of cyclohexanone which comprises reacting cyclohexanone with hydrogen peroxide at a temperature between about $0°$ C. and $100°$ C. in a liquid phase reaction medium in the presence of a catalyst consisting of a zeolite having a Constraint Index between about 0.4-10 and a silica/alumina ratio between about 1-70, and producing a product comprising 6-hydroxycaproic acid.

14. A process in accordance with claim 13 wherein the liquid phase reaction medium includes a water-immiscible organic solvent.

15. A process in accordance with claim 13 wherein the liquid phase reaction medium contains between about 5-30 weight percent of water.

* * * * *